United States Patent
Meng et al.

(10) Patent No.: US 12,378,583 B2
(45) Date of Patent: Aug. 5, 2025

(54) *ESCHERICHIA COLI*-BASED RECOMBINANT STRAIN, CONSTRUCTION METHOD THEREFOR AND USE THEREOF

(71) Applicant: INNER MONGOLIA EPPEN BIOTECH CO., LTD., Inner Mongolia (CN)

(72) Inventors: Gang Meng, Inner Mongolia (CN); Aiying Wei, Inner Mongolia (CN); Huiping Jia, Inner Mongolia (CN); Chunguang Zhao, Inner Mongolia (CN); Xiaoqun Zhou, Inner Mongolia (CN); Fengyong Ma, Inner Mongolia (CN); Xiaowei Guo, Inner Mongolia (CN); Bin Tian, Inner Mongolia (CN); Houbo Su, Inner Mongolia (CN); Lipeng Yang, Inner Mongolia (CN)

(73) Assignee: INNER MONGOLIA EPPEN BIOTECH CO., LTD., Inner Mongolia (CN)

( * ) Notice: Subject to any disclaimer, the term of this patent is extended or adjusted under 35 U.S.C. 154(b) by 595 days.

(21) Appl. No.: 17/753,367

(22) PCT Filed: Aug. 27, 2020

(86) PCT No.: PCT/CN2020/111840
§ 371 (c)(1),
(2) Date: Feb. 28, 2022

(87) PCT Pub. No.: WO2021/037165
PCT Pub. Date: Mar. 4, 2021

(65) Prior Publication Data
US 2022/0315962 A1 Oct. 6, 2022

(30) Foreign Application Priority Data
Aug. 28, 2019 (CN) .......................... 201910804035.3
Sep. 27, 2019 (CN) .......................... 201910927600.5

(51) Int. Cl.
*C12P 13/08* (2006.01)
*C12N 1/20* (2006.01)
*C12N 9/90* (2006.01)
*C12N 15/70* (2006.01)
*C12R 1/19* (2006.01)

(52) U.S. Cl.
CPC .............. *C12P 13/08* (2013.01); *C12N 1/205* (2021.05); *C12N 9/90* (2013.01); *C12N 15/70* (2013.01); *C12Y 504/02007* (2013.01); *C12N 2800/101* (2013.01); *C12R 2001/19* (2021.05)

(58) Field of Classification Search
CPC ........... C12P 13/08; C12N 1/205; C12N 9/90; C12N 15/70; C12N 2800/101; C12Y 504/02007; C12R 2001/19
See application file for complete search history.

(56) References Cited

U.S. PATENT DOCUMENTS 7,229,797 B1 6/2007 Tischer et al.
2002/0061569 A1* 5/2002 Haselbeck ......... A61K 31/7088
435/325

FOREIGN PATENT DOCUMENTS

| CN | 108504613 A | 9/2018 |
| CN | 110592084 A | 12/2019 |
| CN | 110846333 A | 2/2020 |
| WO | 2011156794 A2 | 12/2011 |

OTHER PUBLICATIONS

*Escherichia coli* strain ATCC 98082 chromosome, complete genome. Accession CP034658. Submitted (Dec. 18, 2018) Institute of Plant Physiology and Ecology, Shanghai Institutes for Biological Sciences (SIBS) of Chinese Academy of Sciences (CAS); https://www.ncbi.nlm.nih.gov/nuccore/CP034658.1/ (Year: 2018).*
UniProt ID A0A077ZCB8_TRITR; https://www.uniprot.org/uniprotkb/A0A077ZCB8/entry (Year: 2014).*
Link AJ, Phillips D, Church GM. Methods for generating precise deletions and insertions in the genome of wild-type *Escherichia coli*: application to open reading frame characterization. J Bacteriol. Oct. 1997;179(20):6228-37. doi: 10.1128/jb.179.20.6228-6237.1997. PMID: 9335267; PMCID: PMC179534. (Year: 1997).*
Livshits VA, Zakataeva NP, Aleshin VV, Vitushkina MV. Identification and characterization of the new gene rhtA involved in threonine and homoserine efflux in *Escherichia coli*. Res Microbiol. Mar. 2003;154(2):123-35. doi: 10.1016/S0923-2508(03)00036-6. PMID: 12648727. (Year: 2003).*
Safety and efficacy of l-threonine produced by fermentation using *Escherichia coli* CGMCC 7.232 for all animal species. EFSA J. Oct. 25, 2018;16(10):e05458. doi: 10.2903/j.efsa.2018.5458. PMID: 32625734; PMCID: PMC7009637. (Year: 2018).*
"Fermentative process using *Escherichia coli*"; Research Diclosure, Kenneth Mason Publications, Hampshire, UK, GB; vol. 645, No. 81; Jan. 1, 2018; ISSN. 0374-4353; pp. 1-22.

(Continued)

*Primary Examiner* — Louise W Humphrey
*Assistant Examiner* — Rachel Emily Martin
(74) *Attorney, Agent, or Firm* — NKL Law; Allen Xue

(57) ABSTRACT

The present disclosure discloses an *Escherichia coli*-based genetically-modified recombinant strain, a construction method therefor and use thereof. A mutant gene obtained by subjecting a wild-type deoB gene (ORF sequence is shown in a sequence 3902352-3903575 in GenBank accession No. CP032667.1) and a wild-type rhtA gene promoter sequence PrhtA (shown in a sequence 850520-850871 in GenBank accession No. AP009048.1) of an *E. coli* K12 strain and a derivative strain thereof (such as MG1655 and W3110) to site-directed mutagenesis, and a recombinant strain obtained therefrom can be used for the production of L-threonine, and compared with an unmutated wild-type strain, the obtained strain can produce L-threonine with a higher concentration and has good strain stability, and also has lower production cost as an L-threonine production strain.

11 Claims, No Drawings

Specification includes a Sequence Listing.

(56) References Cited

OTHER PUBLICATIONS

Blattner FR et al., "The complete genome sequence of *Escherichia coli* K-12", Science; vol. 277; Sep. 5, 1997; pp. 1453-1462; Science; vol. 277(5331), DOI: 10.1126/ science. 277.5331.1453; sequence horizontally; pp. 1-6.
Yang, H.L. et al., GenBank: EGU25861.1, NCBI, Aug. 3, 2011,.
Joloba et al.; "Mutations in deoB and deoC alter an extracellular signaling pathway required for activation of the gab operon in *Escherichia coli*"; Fems Microbiology Letters, vol. 228, No. 1, Nov. 7, 2003; ISSN: 0378-1097. pp. 151-157.

\* cited by examiner

SEQUENCE LISTING

<160> NUMBER OF SEQ ID NOS: 22

<210> SEQ ID NO 1
<211> LENGTH: 1224
<212> TYPE: DNA
<213> ORGANISM: Escherichia coli

<400> SEQUENCE: 1

```
atgaaacgtg catttattat ggtgctggac tcattcggca tcggcgctac agaagatgca      60
gaacgctttg gtgacgtcgg ggctgacacc ctgggtcata tcgcagaagc ttgtgccaaa     120
ggcgaagctg ataacggtcg taaaggcccg ctcaatctgc caaatctgac ccgtctgggg     180
ctggcgaaag cacacgaagg ttctaccggt ttcattccgg cgggaatgga cggcaacgct     240
gaagttatcg gcgcgtacgc atgggcgcac gaaatgtcat ccgtaaaga taccccgtct     300 ggtcactggg aaattgccgg tgtcccggtt ctgtttgagt ggggatattt ctccgatcac     360
gaaaacagct tcccgcaaga gctgctggat aaactggtcg aacgcgctaa tctgccgggt     420
tacctcggta actgccactc ttccggtacg gtcattctgg atcaactggg cgaagagcac     480
atgaaaaccg gcaagccgat tttctatacc tccgctgact ccgtgttcca gattgcctgc     540
catgaagaaa ctttcggtct ggataaactc tacgaactgt gcgaaatcgc ccgtgaagag     600
ctgaccaacg gcggctacaa tatcggtcgt gttatcgctc gtccgtttat cggcgacaaa     660
gccggtaact tccagcgtac cggtaaccgt cacgacctgg ctgttgagcc gccagcaccg     720
accgtgctgc agaaactggt tgatgaaaaa cacggccagg tggtttctgt cggtaaaatt     780
gcggacatct acgccaactg cggtatcacc aaaaaagtga aagcgactgg cctggacgcg     840
ctgtttgacg ccaccatcaa agagatgaaa gaagcgggtg ataacaccat cgtcttcacc     900
aacttcgttg acttcgactc ttcctggggc caccgtcgcg acgtcgccgg ttatgccgcg     960
ggtctggaac tgttcgaccg ccgtctgccg gagctgatgt ctctgctgcg cgatgacgac    1020
atcctgatcc tcaccgctga ccacggttgc gatccgacct ggaccggtac tgaccacacg    1080
cgtgaacaca ttccggtact ggtatatggc ccgaaagtaa aaccgggctc actgggtcat    1140
```

-continued

```
cgtgaaacct tcgcggatat cggccagact ctggcaaaat attttggtac ttctgatatg    1200
gaatatggca aagccatgtt ctga                                            1224
```

<210> SEQ ID NO 2
<211> LENGTH: 1224
<212> TYPE: DNA
<213> ORGANISM: Artificial sequence
<220> FEATURE:
<223> OTHER INFORMATION: synthesized

<400> SEQUENCE: 2

```
atgaaacgtg catttattat ggtgctggac tcattcggca tcggcgctac agaagatgca      60
gaacgctttg gtgacgtcgg ggctgacacc ctgggtcata tcgcagaagc ttgtgccaaa     120
ggcgaagctg ataacggtcg taaaggcccg ctcaatctgc caaatctgac ccgtctgggg     180
ctggcgaaag cacacgaagg ttctaccggt ttcattccgg cgggaatgga cggcaacgct     240
gaagttatcg gcgcgtacgc atgggcgcac gaaatgtcat ccgtaaaga taccccgtct      300 ggtcactggg aaattgccgg tgtcccggtt ctgtttgagt ggggatattt ctccgatcac     360
gaaaacagct cccgcaaga gctgctggat aaactggtcg aacgcgctaa ctgccgggt      420 tacctcggta actgccactc ttccggtacg gtcattctgg atcaactggg cgaagagcac     480
atgaaaaccg gcaagccgat tttctatacc tccgctgact ccgtgttcca gattgcctgc     540
catgaagaaa ctttcggtct ggataaactc tacgaactgt gcgaaatcgc ccgtgaagag     600
ctgaccaacg gcggctacaa tatcggtcgt gttatcgctc gtccgtttat cggcgacaaa     660
gccggtaact tccagcgtac cggtaaccgt cacgacctgg ctgttgagcc gccagcaccg     720
accgtgctgc agaaactggt tgatgaaaaa cacggccagg tggtttctgt cggtaaaatt     780
gcggacatct acgccaactg cggtatcacc aaaaaagtga aagcgactgg cctggacgcg     840
ctgtttgacg ccaccatcaa agagatgaaa gaagcgggtg ataacaccat cgtcttcacc     900
aacttcgttg acttcgactc ttcctggggc caccgtcgcg acgtcgccgg ttatgccgcg     960
ggtctggaac tgttcgaccg ccgtctgccg gagctgatgt ctctgctgcg cgatgacgac    1020
atcctgatcc tcaccgctga ccacggttac gatccgacct ggaccggtac tgaccacacg    1080
cgtgaacaca ttccggtact ggtatatggc ccgaaagtaa aaccgggctc actgggtcat    1140
cgtgaaacct tcgcggatat cggccagact ctggcaaaat attttggtac ttctgatatg    1200
gaatatggca aagccatgtt ctga                                            1224
```

<210> SEQ ID NO 3
<211> LENGTH: 407
<212> TYPE: PRT
<213> ORGANISM: Escherichia coli

<400> SEQUENCE: 3

```
Met Lys Arg Ala Phe Ile Met Val Leu Asp Ser Phe Gly Ile Gly Ala
 1               5                  10                  15

Thr Glu Asp Ala Glu Arg Phe Gly Asp Val Gly Ala Asp Thr Leu Gly
                20                  25                  30

His Ile Ala Glu Ala Cys Ala Lys Gly Glu Ala Asp Asn Gly Arg Lys
            35                  40                  45

Gly Pro Leu Asn Leu Pro Asn Leu Thr Arg Leu Gly Leu Ala Lys Ala
        50                  55                  60

His Glu Gly Ser Thr Gly Phe Ile Pro Ala Gly Met Asp Gly Asn Ala
65                  70                  75                  80
```

Glu Val Ile Gly Ala Tyr Ala Trp Ala His Glu Met Ser Ser Gly Lys
                85                  90                  95

Asp Thr Pro Ser Gly His Trp Glu Ile Ala Gly Val Pro Val Leu Phe
            100                 105                 110

Glu Trp Gly Tyr Phe Ser Asp His Glu Asn Ser Phe Pro Gln Glu Leu
        115                 120                 125

Leu Asp Lys Leu Val Glu Arg Ala Asn Leu Pro Gly Tyr Leu Gly Asn
    130                 135                 140

Cys His Ser Ser Gly Thr Val Ile Leu Asp Gln Leu Gly Glu Glu His
145                 150                 155                 160

Met Lys Thr Gly Lys Pro Ile Phe Tyr Thr Ser Ala Asp Ser Val Phe
                165                 170                 175

Gln Ile Ala Cys His Glu Glu Thr Phe Gly Leu Asp Lys Leu Tyr Glu
            180                 185                 190

Leu Cys Glu Ile Ala Arg Glu Glu Leu Thr Asn Gly Gly Tyr Asn Ile
        195                 200                 205

Gly Arg Val Ile Ala Arg Pro Phe Ile Gly Asp Lys Ala Gly Asn Phe
    210                 215                 220

Gln Arg Thr Gly Asn Arg His Asp Leu Ala Val Glu Pro Pro Ala Pro
225                 230                 235                 240

Thr Val Leu Gln Lys Leu Val Asp Glu Lys His Gly Gln Val Val Ser
                245                 250                 255

Val Gly Lys Ile Ala Asp Ile Tyr Ala Asn Cys Gly Ile Thr Lys Lys
            260                 265                 270

Val Lys Ala Thr Gly Leu Asp Ala Leu Phe Asp Ala Thr Ile Lys Glu
        275                 280                 285

Met Lys Glu Ala Gly Asp Asn Thr Ile Val Phe Thr Asn Phe Val Asp
    290                 295                 300

Phe Asp Ser Ser Trp Gly His Arg Arg Asp Val Ala Gly Tyr Ala Ala
305                 310                 315                 320

Gly Leu Glu Leu Phe Asp Arg Arg Leu Pro Glu Leu Met Ser Leu Leu
                325                 330                 335

Arg Asp Asp Asp Ile Leu Ile Leu Thr Ala Asp His Gly Cys Asp Pro
            340                 345                 350

Thr Trp Thr Gly Thr Asp His Thr Arg Glu His Ile Pro Val Leu Val
        355                 360                 365

Tyr Gly Pro Lys Val Lys Pro Gly Ser Leu Gly His Arg Glu Thr Phe
    370                 375                 380

Ala Asp Ile Gly Gln Thr Leu Ala Lys Tyr Phe Gly Thr Ser Asp Met
385                 390                 395                 400

Glu Tyr Gly Lys Ala Met Phe
                405

<210> SEQ ID NO 4
<211> LENGTH: 407
<212> TYPE: PRT
<213> ORGANISM: Artificial sequence
<220> FEATURE:
<223> OTHER INFORMATION: synthesized

<400> SEQUENCE: 4

Met Lys Arg Ala Phe Ile Met Val Leu Asp Ser Phe Gly Ile Gly Ala
1               5                   10                  15

Thr Glu Asp Ala Glu Arg Phe Gly Asp Val Gly Ala Asp Thr Leu Gly
            20                  25                  30

His Ile Ala Glu Ala Cys Ala Lys Gly Glu Ala Asp Asn Gly Arg Lys
            35                  40                  45

Gly Pro Leu Asn Leu Pro Asn Leu Thr Arg Leu Gly Leu Ala Lys Ala
     50                  55                  60

His Glu Gly Ser Thr Gly Phe Ile Pro Ala Gly Met Asp Gly Asn Ala
 65                  70                  75                  80

Glu Val Ile Gly Ala Tyr Ala Trp Ala His Glu Met Ser Ser Gly Lys
                 85                  90                  95

Asp Thr Pro Ser Gly His Trp Glu Ile Ala Gly Val Pro Val Leu Phe
            100                 105                 110

Glu Trp Gly Tyr Phe Ser Asp His Glu Asn Ser Phe Pro Gln Glu Leu
            115                 120                 125

Leu Asp Lys Leu Val Glu Arg Ala Asn Leu Pro Gly Tyr Leu Gly Asn
    130                 135                 140

Cys His Ser Ser Gly Thr Val Ile Leu Asp Gln Leu Gly Glu Glu His
145                 150                 155                 160

Met Lys Thr Gly Lys Pro Ile Phe Tyr Thr Ser Ala Asp Ser Val Phe
                165                 170                 175

Gln Ile Ala Cys His Glu Glu Thr Phe Gly Leu Asp Lys Leu Tyr Glu
            180                 185                 190

Leu Cys Glu Ile Ala Arg Glu Glu Leu Thr Asn Gly Gly Tyr Asn Ile
        195                 200                 205

Gly Arg Val Ile Ala Arg Pro Phe Ile Gly Asp Lys Ala Gly Asn Phe
    210                 215                 220

Gln Arg Thr Gly Asn Arg His Asp Leu Ala Val Glu Pro Pro Ala Pro
225                 230                 235                 240

Thr Val Leu Gln Lys Leu Val Asp Glu Lys His Gly Gln Val Val Ser
                245                 250                 255

Val Gly Lys Ile Ala Asp Ile Tyr Ala Asn Cys Gly Ile Thr Lys Lys
            260                 265                 270

Val Lys Ala Thr Gly Leu Asp Ala Leu Phe Asp Ala Thr Ile Lys Glu
        275                 280                 285

Met Lys Glu Ala Gly Asp Asn Thr Ile Val Phe Thr Asn Phe Val Asp
    290                 295                 300

Phe Asp Ser Ser Trp Gly His Arg Arg Asp Val Ala Gly Tyr Ala Ala
305                 310                 315                 320

Gly Leu Glu Leu Phe Asp Arg Arg Leu Pro Glu Leu Met Ser Leu Leu
                325                 330                 335

Arg Asp Asp Asp Ile Leu Ile Leu Thr Ala Asp His Gly Tyr Asp Pro
            340                 345                 350

Thr Trp Thr Gly Thr Asp His Thr Arg Glu His Ile Pro Val Leu Val
        355                 360                 365

Tyr Gly Pro Lys Val Lys Pro Gly Ser Leu Gly His Arg Glu Thr Phe
    370                 375                 380

Ala Asp Ile Gly Gln Thr Leu Ala Lys Tyr Phe Gly Thr Ser Asp Met
385                 390                 395                 400

Glu Tyr Gly Lys Ala Met Phe
                405

<210> SEQ ID NO 5
<211> LENGTH: 27
<212> TYPE: DNA
<213> ORGANISM: Artificial sequence
<220> FEATURE:

```
<223> OTHER INFORMATION: synthesized

<400> SEQUENCE: 5
cgggatccat ggacggcaac gctgaag                                           27

<210> SEQ ID NO 6
<211> LENGTH: 18
<212> TYPE: DNA
<213> ORGANISM: Artificial sequence
<220> FEATURE:
<223> OTHER INFORMATION: synthesized

<400> SEQUENCE: 6
gatcgtaacc gtggtcag                                                     18

<210> SEQ ID NO 7
<211> LENGTH: 18
<212> TYPE: DNA
<213> ORGANISM: Artificial sequence
<220> FEATURE:
<223> OTHER INFORMATION: synthesized

<400> SEQUENCE: 7
ctgaccacgg ttacgatc                                                     18

<210> SEQ ID NO 8
<211> LENGTH: 36
<212> TYPE: DNA
<213> ORGANISM: Artificial sequence
<220> FEATURE:
<223> OTHER INFORMATION: synthesized

<400> SEQUENCE: 8
aaggaaaaaa gcggccgcgc tcgtgagtgc ggatgt                                 36

<210> SEQ ID NO 9
<211> LENGTH: 20
<212> TYPE: DNA
<213> ORGANISM: Artificial sequence
<220> FEATURE:
<223> OTHER INFORMATION: synthesized

<400> SEQUENCE: 9
tgacgccacc atcaaagaga                                                   20

<210> SEQ ID NO 10
<211> LENGTH: 19
<212> TYPE: DNA
<213> ORGANISM: Artificial sequence
<220> FEATURE:
<223> OTHER INFORMATION: synthesized

<400> SEQUENCE: 10
gtcaacgctc cgcccaaat                                                    19

<210> SEQ ID NO 11
<211> LENGTH: 1684
<212> TYPE: DNA
<213> ORGANISM: Artificial sequence
<220> FEATURE:
<223> OTHER INFORMATION: synthesized

<400> SEQUENCE: 11
gacggcaacg ctgaagttat cggcgcgtac gcatgggcgc acgaaatgtc atccggtaaa       60 gatacccccgt ctggtcactg ggaaattgcc ggtgtcccgg ttctgtttga gtggggatat     120
```

```
ttctccgatc acgaaaacag cttcccgcaa gagctgctgg ataaactggt cgaacgcgct      180
aatctgccgg gttacctcgg taactgccac tcttccggta cggtcattct ggatcaactg      240
ggcgaagagc acatgaaaac cggcaagccg attttctata cctccgctga ctccgtgttc      300
cagattgcct gccatgaaga aactttcggt ctggataaac tctacgaact gtgcgaaatc      360
gcccgtgaag agctgaccaa cggcggctac aatatcggtc gtgttatcgc tcgtccgttt      420
atcggcgaca aagccggtaa cttccagcgt accggtaacc gtcacgacct ggctgttgag      480
ccgccagcac cgaccgtgct gcagaaactg gttgatgaaa acacggcca ggtggttcct      540 gtcggtaaaa ttgcggacat ctacgccaac tgcggtatca ccaaaaagt gaaagcgact      600 ggcctggacg cgctgtttga cgccaccatc aaagagatga agaagcggg tgataacacc      660 atcgtcttca ccaacttcgt tgacttcgac tcttcctggg ccaccgtcg cgacgtcgcc      720 ggttatgccg cgggtctgga actgttcgac cgccgtctgc cggagctgat gtctctgctg      780
cgcgatgacg acatcctgat cctcaccgct gaccacggtt acgatccgac ctggaccggt      840
actgaccaca cgcgtgaaca cattccggta ctggtatatg gcccgaaagt aaaaccgggc      900
tcactgggtc atcgtgaaac cttcgcggat atcggccaga ctctggcaaa atattttggt      960
acttctgata tggaatatgg caaagccatg ttctgatgga tttgggcgga gcgttgactc     1020
cgcctttgtt atgtcacaaa aaggataaaa caatggctac cccacacatt aatgcagaaa     1080
tgggcgattt cgctgacgta gttttgatgc caggcgaccc gctgcgtgcg aagtatattg     1140
ctgaaacttt ccttgaagat gcccgtgaag tgaacaacgt tcgcggtatg ctgggcttca     1200
ccggtactta caaaggccgc aaaatttccg taatgggtca cggtatgggt atcccgtcct     1260
gctccatcta caccaaagaa ctgatcaccg atttcggcgt gaagaaaatt atccgcgtgg     1320
gttcctgtgg cgcagttctg ccgcacgtaa aactgcgcga cgtcgttatc ggtatgggtg     1380
cctgcaccga ttccaaagtt aaccgcatcc gttttaaaga ccatgacttt gccgctatcg     1440
ctgacttcga catggtgcgt aacgcagtag atgcagctaa agcactgggt attgatgctc     1500
gcgtgggtaa cctgttctcc gctgacctgt tctactctcc ggacggcgaa atgttcgacg     1560
tgatggaaaa atacggcatt ctcggcgtgg aaatggaagc ggctggtatc tacgcgtcg     1620 ctgcagaatt tggcgcgaaa gccctgacca tctgcaccgt atctgaccac atccgcactc     1680
acga                                                                 1684
```

<210> SEQ ID NO 12
<211> LENGTH: 401
<212> TYPE: DNA
<213> ORGANISM: Artificial sequence
<220> FEATURE:
<223> OTHER INFORMATION: synthesized

<400> SEQUENCE: 12

```
tgacgccacc atcaaagaga tgaaagaagc gggtgataac accatcgtct tcaccaactt       60
cgttgacttc gactcttcct ggggccaccg tcgcgacgtc gccggttatg ccgcgggtct      120
ggaactgttc gaccgccgtc tgccggagct gatgtctctg ctgcgcgatg acgacatcct      180
gatcctcacc gctgaccacg gttacgatcc gacctggacc ggtactgacc acacgcgtga      240
acacattccg gtactggtat atggcccgaa agtaaaaccg ggctcactgg gtcatcgtga      300
aaccttcgcg gatatcggcc agactctggc aaaatatttt ggtacttctg atatggaata      360
tggcaaagcc atgttctgat ggatttgggc ggagcgttga c                         401
```

<210> SEQ ID NO 13
<211> LENGTH: 355
<212> TYPE: DNA
<213> ORGANISM: Artificial sequence
<220> FEATURE:
<223> OTHER INFORMATION: synthesized

<400> SEQUENCE: 13

```
cataaccacc tcaaatgtga ttcaaataag tcctaagttt taaatatatc aaaaattaat      60
gggaaactct tcgcgatttg tgatgtctaa cgggccattt catgtaacag aacgtttcca     120
tacaccgcta tccatctaaa tttaaatcac ttttttcagag aactgcgtaa gtattacgca    180
tgttttccct gtcattcatc cagattattc ctaatcacca gactaatgat tccatcaatc    240
ctggcgcatt ttagtcaaaa cgggggaaaa ttttttcaac aaatgctcaa ccagcattgg    300
gtatatccag tacactccac gctttactta agtctagata tttgtgggag aaagg          355
```

<210> SEQ ID NO 14
<211> LENGTH: 355
<212> TYPE: DNA
<213> ORGANISM: Artificial sequence
<220> FEATURE:
<223> OTHER INFORMATION: synthesized

<400> SEQUENCE: 14

```
cataaccacc tcaaatgtga ttcaaataag tcctaagttt taaatatatc aaaaattaat      60
gggaaactct tcgcgatttg tgatgtctaa cgggccattt catgtaacag aacgtttcca     120
tacaccgcta tccatctaaa tttaaatcac ttttttcagag aactgcgtaa gtattacgca    180
tgttttccct gtcattcatc cagattattc ctaatcacca gactaatgat tccatcaatc    240
ctggcgcatt ttagtcaaaa cgggggaaaa ttttttcaac aaatgctcga ccagcattgg    300
gtatatccag tacactccac gctttactta agtctagata tttgtgggag aaagg          355
```

<210> SEQ ID NO 15
<211> LENGTH: 888
<212> TYPE: DNA
<213> ORGANISM: Escherichia coli

<400> SEQUENCE: 15

```
atgcctggtt cattacgtaa aatgccggtc tggttaccaa tagtcatatt gctcgttgcc      60
atggcgtcta ttcagggtgg agcctcgtta gctaagtcac ttttttcctct ggtgggcgca    120
ccgggtgtca ctgcgctgcg tctggcatta ggaacgctga tcctcatcgc gttctttaag    180
ccatggcgac tgcgctttgc caaagagcaa cggttaccgc tgttgtttta cggcgtttcg    240
ctgggtggga tgaattatct ttttttatctt tctattcaga cagtaccgct gggtattgcg    300
gtggcgctgg agttcaccgg accactggcg gtggcgctgt tctcttctcg tcgcccggta    360
gatttcgtct gggttgtgct ggcggttctt ggtctgtggt tcctgctacc gctggggcaa    420
gacgtttccc atgtcgattt aaccggctgt gcgctggcac tggggccgg gcttgttgg     480
gctatttaca ttttaagtgg gcaacgcgca ggagcggaac atggccctgc gacggtggca    540
attggtcgt tgattgcagc gttaattttc gtgccaattg gagcgcttca ggctggtgaa    600
gcactctggc actggtcggt tattccattg gtctggctg tcgctattct ctcgaccgct    660
ctgccttatt cgctggaaat gattgccctc acccgtttgc caacacggac atttggtacg    720
ctgatgagca tggaaccggc gctggctgcc gtttccggga tgattttcct cggagaaaca    780
ctgacaccca tacagctact ggcgctcggc gctatcatcg ccgcttcaat ggggtctacg    840
```
ctgacagtac gcaaagagag caaaataaaa gaattagaca ttaattaa        888

<210> SEQ ID NO 16
<211> LENGTH: 295
<212> TYPE: PRT
<213> ORGANISM: Escherichia coli

<400> SEQUENCE: 16

Met Pro Gly Ser Leu Arg Lys Met Pro Val Trp Leu Pro Ile Val Ile
1               5                   10                  15

Leu Leu Val Ala Met Ala Ser Ile Gln Gly Gly Ala Ser Leu Ala Lys
            20                  25                  30

Ser Leu Phe Pro Leu Val Gly Ala Pro Gly Val Thr Ala Leu Arg Leu
        35                  40                  45

Ala Leu Gly Thr Leu Ile Leu Ile Ala Phe Phe Lys Pro Trp Arg Leu
    50                  55                  60

Arg Phe Ala Lys Glu Gln Arg Leu Pro Leu Leu Phe Tyr Gly Val Ser
65                  70                  75                  80

Leu Gly Gly Met Asn Tyr Leu Phe Tyr Leu Ser Ile Gln Thr Val Pro
                85                  90                  95

Leu Gly Ile Ala Val Ala Leu Glu Phe Thr Gly Pro Leu Ala Val Ala
            100                 105                 110

Leu Phe Ser Ser Arg Arg Pro Val Asp Phe Val Trp Val Val Leu Ala
        115                 120                 125

Val Leu Gly Leu Trp Phe Leu Leu Pro Leu Gly Gln Asp Val Ser His
    130                 135                 140

Val Asp Leu Thr Gly Cys Ala Leu Ala Leu Gly Ala Gly Ala Cys Trp
145                 150                 155                 160

Ala Ile Tyr Ile Leu Ser Gly Gln Arg Ala Gly Ala Glu His Gly Pro
                165                 170                 175

Ala Thr Val Ala Ile Gly Ser Leu Ile Ala Ala Leu Ile Phe Val Pro
            180                 185                 190

Ile Gly Ala Leu Gln Ala Gly Glu Ala Leu Trp His Trp Ser Val Ile
        195                 200                 205

Pro Leu Gly Leu Ala Val Ala Ile Leu Ser Thr Ala Leu Pro Tyr Ser
    210                 215                 220

Leu Glu Met Ile Ala Leu Thr Arg Leu Pro Thr Arg Thr Phe Gly Thr
225                 230                 235                 240

Leu Met Ser Met Glu Pro Ala Leu Ala Ala Val Ser Gly Met Ile Phe
                245                 250                 255

Leu Gly Glu Thr Leu Thr Pro Ile Gln Leu Leu Ala Leu Gly Ala Ile
            260                 265                 270

Ile Ala Ala Ser Met Gly Ser Thr Leu Thr Val Arg Lys Glu Ser Lys
        275                 280                 285

Ile Lys Glu Leu Asp Ile Asn
    290                 295

<210> SEQ ID NO 17
<211> LENGTH: 30
<212> TYPE: DNA
<213> ORGANISM: Artificial sequence
<220> FEATURE:
<223> OTHER INFORMATION: synthesized

<400> SEQUENCE: 17
cgggatcctc gctggtgtcg tgtttgtagg                              30

```
<210> SEQ ID NO 18
<211> LENGTH: 20
<212> TYPE: DNA
<213> ORGANISM: Artificial sequence
<220> FEATURE:
<223> OTHER INFORMATION: synthesized

<400> SEQUENCE: 18
tatacccaat gctggtcgag                                             20

<210> SEQ ID NO 19
<211> LENGTH: 20
<212> TYPE: DNA
<213> ORGANISM: Artificial sequence
<220> FEATURE:
<223> OTHER INFORMATION: synthesized

<400> SEQUENCE: 19
cgaccagcat tgggtatatc                                             20

<210> SEQ ID NO 20
<211> LENGTH: 41
<212> TYPE: DNA
<213> ORGANISM: Artificial sequence
<220> FEATURE:
<223> OTHER INFORMATION: synthesized

<400> SEQUENCE: 20
aaggaaaaaa gcggccgccg aaaattaacg ctgcaatcaa c                     41

<210> SEQ ID NO 21
<211> LENGTH: 18
<212> TYPE: DNA
<213> ORGANISM: Artificial sequence
<220> FEATURE:
<223> OTHER INFORMATION: synthesized

<400> SEQUENCE: 21
atacaccgct atccatct                                               18

<210> SEQ ID NO 22
<211> LENGTH: 18
<212> TYPE: DNA
<213> ORGANISM: Artificial sequence
<220> FEATURE:
<223> OTHER INFORMATION: synthesized

<400> SEQUENCE: 22
aaccaggcat cctttctc                                               18
```

ESCHERICHIA COLI-BASED RECOMBINANT STRAIN, CONSTRUCTION METHOD THEREFOR AND USE THEREOF

CROSS-REFERENCE TO RELATED APPLICATIONS

This application is a U.S. national stage application of PCT International Application No. PCT/CN2020/111840, filed on Aug. 27, 2020, which claims priority to Chinese Patent Application No. 2019109276005, filed with China National Intellectual Property Administration on Sep. 27, 2019, and Chinese Patent Application No. 2019108040353, filed on Aug. 28, 2019, the contents of which are incorporated herein by reference in their entireties.

INCORPORATION OF SEQUENCE LISTING

This application contains a sequence listing submitted in Computer Readable Form (CRF). The CFR file containing the sequence listing entitled "PA150-0141_ST25.txt", which was created on Feb. 28, 2022, and is 21,177 bytes in size. The information in the sequence listing is incorporated herein by reference in its entirety.

TECHNICAL FIELD

The present disclosure relates to the technical field of genetic engineering and microorganisms, and in particular to an *Escherichia coli*-based recombinant strain, a construction method therefor and use thereof.

BACKGROUND

L-threonine is one of the eight essential amino acids, and is an amino acid that humans and animals cannot synthesize on their own. L-threonine can strengthen the absorption of grains, regulate the metabolism balance in vivo and promote the growth and development of organisms, and thus is widely applied to the feed, medicine and food industries.

At present, L-threonine can be produced mainly via a chemical synthesis method, a protein hydrolysis method and a microbial fermentation method, wherein the microbial fermentation method has the advantages of low production cost, high production intensity and small environmental pollution, thereby becoming the most widely applied method for industrially producing L-threonine. Various bacteria can be used for microbial fermentation production of L-threonine, such as mutants obtained by wild-type induction of *Escherichia coli* (*E. coli*), Corynebacterium, and Serratia, as production strains. Specific examples include amino acid analogue resistant mutants or various auxotrophs, such as methionine, threonine, and isoleucine. However, in the conventional mutation breeding, the strain grows slowly and generates more byproducts due to random mutation, so that a high-yield strain is not easy to obtain. Therefore, the construction of recombinant *E. coli* by metabolic engineering is an effective way to produce L-threonine. At present, overexpression or attenuation of key enzyme genes in the amino acid synthesis pathway and the competitive pathway mediated by expression plasmids is a main means for genetic modification of *E. coli*. There is still a need to develop a method for producing L-threonine more economically with a high yield.

*E. coli*, as a host for exogenous gene expression, has the advantages of clear genetic background, simple technical operation and culture conditions and economic large-scale fermentation, and thus is paid more attention by genetic engineering experts. The genome DNA of *E. coli* is a circular molecule in a nucleoid, and a plurality of circular plasmid DNAs can also be provided. A nucleoid in cells of *E. coli* has one DNA molecule with a length of about 4,700,000 base pairs, and have about 4400 genes distributed on the DNA molecule, with each gene having an average length of about 1000 base pairs. For the strains of *E. coli* commonly used in molecular biology, the most commonly used strains in DNA recombination experiments, with a few exceptions, are an *E. coli* K12 strain and a derivative thereof.

SUMMARY

The present disclosure provides an *Escherichia coli* strain K12-based recombinant strain or a derivative strain thereof, a recombinant construction method therefor and use thereof in the fermentation production of an amino acid.

The present disclosure focuses on a wild-type deoB gene (ORF sequence is shown in a sequence 3902352-3903575 in GenBank accession No. CP032667.1) and a wild-type rhtA gene promoter sequence PrhtA (shown in a sequence 850520-850871 in GenBank accession No. AP009048.1) of an *E. coli* K12 strain and a derivative strain thereof (such as MG1655 and W3110), and finds that a mutant gene obtained by subjecting the gene to site-directed mutagenesis and a recombinant strain comprising the mutant gene can be used for the production of L-threonine, and compared with an unmutated wild-type strain, the obtained strain can greatly improve the yield of L-threonine and has good strain stability, and also has lower production cost and increased production efficiency as an L-threonine production strain.

Based on the above disclosures, the present disclosure provides the following two technical solutions: For the first technical solution, provided is a nucleotide sequence comprising a sequence formed by a mutation occurring at the $1049^{th}$ base of a coding sequence of a wild-type deoB gene shown in SEQ ID NO: 1.

According to the present disclosure, the mutation refers to a change in a base/nucleotide at the site, and the mutation method may be at least one selected from mutagenesis, PCR site-directed mutagenesis, and/or homologous recombination, and the like.

According to the present disclosure, the mutation is that guanine (G) mutates to adenine (A) at the $1049^{th}$ base in SEQ ID NO: 1; specifically, the mutated nucleotide sequence is shown in SEQ ID NO: 2.

The present disclosure also provides a recombinant protein encoded by the above-mentioned nucleotide sequence.

The recombinant protein disclosed herein comprises an amino acid sequence shown in SEQ ID NO: 4.

The present disclosure also provides a recombinant vector comprising the above-mentioned nucleotide sequence.

The recombinant vector disclosed herein is constructed by introducing the above-mentioned nucleotide sequence into a plasmid; as an embodiment, the plasmid is a pKOV plasmid. Specifically, the nucleotide sequence and the plasmid may be digested with an endonuclease to form complementary cohesive ends which are ligated to construct a recombinant vector.

The present disclosure also provides a recombinant strain, which comprises a deoB gene coding nucleotide sequence with a point mutation occurring at the coding sequence.

The recombinant strain disclosed herein contains the above-mentioned mutated nucleotide sequence.

As an embodiment of the present disclosure, the recombinant strain contains the nucleotide sequence shown in SEQ ID NO: 2.

As an embodiment of the present disclosure, the recombinant strain contains the amino acid sequence shown in SEQ ID NO: 4.

The recombinant strain disclosed herein is formed by introducing the above-mentioned recombinant vector into a host strain; the host strain is not particularly defined, and may be selected from a L-threonine production strain known in the art that retains the deoB gene, for example, from *Escherichia coli*. As an embodiment of the present disclosure, the host strain is an *E. coli* K12 (W3110) strain, or an *E. coli* CGMCC 7.232 strain.

The recombinant strain disclosed herein takes a pKOV plasmid as a vector.

The recombinant strain disclosed herein may further comprise other modifications.

The present disclosure also provides a construction method for a recombinant strain, which comprises the following step:

modifying a nucleotide sequence of an open reading frame region of a wild-type deoB gene shown in SEQ ID NO: 1 to enable a mutation to occur at the 1049$^{th}$ base of the sequence so as to obtain a L-threonine production recombinant strain comprising the mutated deoB coding gene.

According to the construction method of the present disclosure, the modification comprises at least one of mutagenesis, PCR site-directed mutagenesis, and/or homologous recombination, and the like.

According to the construction method of the present disclosure, the mutation is that guanine (G) mutates to adenine (A) at the 1049$^{th}$ base in SEQ ID NO: 1; specifically, the mutated nucleotide sequence is shown in SEQ ID NO: 2.

Illustratively, the construction method comprises the following steps:

(1) modifying a nucleotide sequence of an open reading frame region of a wild-type deoB gene shown in SEQ ID NO: 1 to enable a mutation to occur at the 1049$^{th}$ base of the sequence so as to obtain a mutated nucleotide sequence of an open reading frame region of the deoB gene;

(2) ligating the mutated nucleotide sequence to a plasmid to construct a recombinant vector; and (3) introducing the recombinant vector into a host strain to obtain the L-threonine production recombinant strain having a point mutation.

According to the construction method of the present disclosure, the step (1) comprises: the construction of the deoB gene coding region having a point mutation, namely comprising synthesizing two pairs of primers for amplifying deoB gene coding region fragments according to the deoB gene coding sequence, and introducing the point mutation in the wild-type deoB gene coding region (SEQ ID NO: 1) by PCR site-directed mutagenesis to obtain a nucleotide sequence (SEQ ID NO: 2) of the deoB gene coding region having the point mutation, wherein the nucleotide sequence is marked as deoB$^{(G1049A)}$.

In an embodiment of the present disclosure, in the step (1), the primers are:

```
P1:
                                        (SEQ ID NO: 5)
5' CGGGATCCATGGACGGCAACGCTGAAG 3'
(the underlined part is a restriction endonuclease
cutting site BamH I);

P2:
                                        (SEQ ID NO: 6)
5' GATCGTAACCGTGGTCAG 3';

P3:
                                        (SEQ ID NO: 7)
5' CTGACCACGGTTACGATC 3';
and P4:
                                        (SEQ ID NO: 8)
5'AAGGAAAAAAGCGGCCGCGCTCGTGAGTGCGGATGT 3'
(the underlined part is a restriction endonuclease
cutting site Not I).
```

In an embodiment of the present disclosure, the step (1) comprises: using primers P1/P2 and P3/P4 for PCR amplification by taking *E. coli* K12 as a template to obtain two isolated DNA fragments (deoB Up and deoB Down) having a length of 836 bp and 890 bp and deoB gene coding regions; and separating and purifying the two DNA fragments by agarose gel electrophoresis, and then performing overlap PCR by taking P1 and P4 as primers and taking the two DNA fragments as templates to obtain deoB$^{(G1049A)}$-Up-Down.

In an embodiment of the present disclosure, the nucleotide sequence of the deoB$^{(G1049A)}$-Up-Down has a length of 1726 bp.

In an embodiment of the present disclosure, the PCR amplification is performed as follows: denaturing at 94° C. for 30 s, annealing at 52° C. for 30 s, and extending at 72° C. for 30 s (for 30 cycles).

In an embodiment of the present disclosure, the overlap PCR amplification is performed as follows: denaturing at 94° C. for 30 s, annealing at 52° C. for 30 s, and extending at 72° C. for 60 s (for 30 cycles).

According to the construction method of the present disclosure, the step (2) comprises: the construction of the recombinant vector, namely comprising separating and purifying the deoB$^{(G1049A)}$-Up-Down fragment by agarose gel electrophoresis, then double digesting the purified fragment and the pKOV plasmid with BamH I/Not I, and separating and purifying the digested deoB$^{(G1049A)}$-Up-Down fragment and the digested pKOV plasmid by agarose gel electrophoresis followed by ligation to obtain the recombinant vector pKOV-deoB$^{(G1049A)}$.

According to the construction method of the present disclosure, the step (3) comprises: the construction of the recombinant strain, namely comprising transforming the recombinant vector pKOV-deoB$^{(G1049A)}$ into the host strain to obtain the recombinant strain.

In an embodiment of the present disclosure, the transformation in the step (3) is an electrotransformation process; illustratively, in the step (3), the recombinant vector is introduced into the host strain.

According to the construction method of the present disclosure, the method further comprises a step of screening the recombinant strain; illustratively, screening is performed by using a chloramphenicol culture medium.

The present disclosure also provides a recombinant strain obtained by the above-mentioned construction method.

The present disclosure also provides use of the above-mentioned recombinant strain in the preparation of L-threonine or the improvement of L-threonine fermentation volume.

The use of the recombinant strain in the preparation of L-threonine comprises fermenting the recombinant strain to prepare L-threonine.

For the second technical solution, provided is a promoter comprising a nucleotide sequence formed by a mutation occurring at the −67$^{th}$ base at the upstream of a nucleotide sequence shown in SEQ ID NO: 13.

According to the present disclosure, the mutation refers to a change in a base at the site, and the mutation method may be at least one selected from mutagenesis, PCR site-directed mutagenesis, and/or homologous recombination, and the like.

According to the present disclosure, the mutation is that adenine (A) mutates to guanine (G) at the −67$^{th}$ base in SEQ ID NO: 13; specifically, the mutated promoter nucleotide sequence is shown in SEQ ID NO: 14.

The present disclosure provides an expression cassette, which comprises the above-mentioned promoter and a coding nucleotide sequence of a rhtA gene. As an embodiment of the present disclosure, the promoter is located at the 5' upstream of the coding nucleotide sequence of the rhtA gene, constituting an expression cassette.

According to the expression cassette of the present disclosure, the coding nucleotide sequence of the rhtA gene comprises the nucleotide sequence shown in SEQ ID NO: 15, and the nucleotide sequence encodes a sequence comprising an amino acid sequence shown in SEQ ID NO: 16.

The present disclosure provides a recombinant vector, which comprises the above-mentioned promoter.

The recombinant vector disclosed herein is constructed by introducing the nucleotide sequence comprising the above-mentioned promoter nucleotide sequence into a plasmid; as an embodiment, the plasmid is a pKOV plasmid. Specifically, the nucleotide sequence comprising the promoter nucleotide sequence and the plasmid may be digested with an endonuclease to form complementary cohesive ends which are ligated to construct a recombinant vector.

The present disclosure also provides a recombinant strain, which comprises the above-mentioned promoter.

The recombinant strain disclosed herein comprises a promoter nucleotide sequence shown in SEQ ID NO: 14; furthermore, the recombinant strain comprises the above-mentioned expression cassette.

The recombinant strain disclosed herein is formed by introducing the above-mentioned recombinant vector into a host strain; the host strain is not particularly defined, and may be selected from a L-threonine production strain known in the art that retains the rhtA gene, for example, from *Escherichia coli*. As an embodiment of the present disclosure, the host strain is *E. coli* K12, or a derivative strain thereof *E. coli* K12 (W3110), or an *E. coli* CGMCC 7.232 strain.

The recombinant strain disclosed herein takes a pKOV plasmid as a vector.

The recombinant strain according to the present disclosure may or may not further comprise other modifications.

The present disclosure also provides a construction method for a recombinant strain, which comprises the following step:

modifying a promoter region shown in SEQ ID NO: 13 to enable a mutation to occur at the −67$^{th}$ base of the region so as to obtain a promoter recombinant strain having a point mutation.

According to the construction method of the present disclosure, the modification comprises at least one of mutagenesis, PCR site-directed mutagenesis, and/or homologous recombination, and the like.

According to the construction method of the present disclosure, the mutation is that adenine (A) mutates to guanine (G) at the −67$^{th}$ base in SEQ ID NO: 13; specifically, the promoter nucleotide sequence of the rhtA gene with the point mutation is shown in SEQ ID NO: 14.

Furthermore, the construction method comprises the following steps:
(1) modifying a wild-type promoter region of the rhtA gene shown in SEQ ID NO: 13 to enable a mutation to occur at the −67$^{th}$ base of the region so as to obtain a nucleotide sequence of the mutated promoter region;
(2) ligating the nucleotide sequence of the mutated promoter region to a plasmid to construct a recombinant vector; and
(3) introducing the recombinant vector into a host strain to obtain a recombinant strain comprising the mutated promoter region.

According to the present disclosure, in the step (1), the method for the mutation of the base comprises mutagenesis, PCR site-directed mutagenesis or homologous recombination, and preferably the PCR site-directed mutagenesis.

According to the present disclosure, the step (1) comprises:

synthesizing two pairs of primers for amplifying rhtA gene promoter region fragments according to the wild-type rhtA gene promoter sequence in GenBank, and replacing a rhtA gene promoter region in the host strain with alleles.

In an embodiment of the present disclosure, the primers are:

P1:
                                        (SEQ ID NO: 17)
5' CGGGATCCTCGCTGGTGTCGTGTTTGTAGG 3'
(the underlined part is a restriction endonuclease cutting site BamH I);

P2:
                                        (SEQ ID NO: 18)
5' TATACCCAATGCTGGTCGAG 3';

P3:
                                        (SEQ ID NO: 19)
5' CGACCAGCATTGGGTATATC 3';
and P4:
                                        (SEQ ID NO: 20)
5' AAGGAAAAAAGCGGCCGCCGAAAATTAACGCTGCAATCAAC 3'
(the underlined part is a restriction endonuclease cutting site Not I).

In an embodiment of the present disclosure, the step (1) comprises: using primers P1/P2 and P3/P4 for PCR amplification by taking *E. coli* K12 as a template to obtain two isolated DNA fragments having a length of 690 bp and 640 bp and rhtA gene promoter regions, namely PrhtA$^{(A(-67)G)}$-Up and PrhtA$^{(A(-67)G)}$-Down fragments; and then performing overlap PCR by taking P1 and P4 as primers and taking the two DNA fragments as templates to obtain a PrhtA$^{(A(-67)G)}$-Up-Down fragment, wherein the overlap PCR amplification is performed as follows: denaturing at 94° C. for 30 s, annealing at 52° C. for 30 s, and extending at 72° C. for 60 s (for 30 cycles).

According to the present disclosure, the step (2) comprises: separating and purifying the PrhtA$^{(A(-67)G)}$-Up- Down fragment by agarose gel electrophoresis, then double digesting the purified fragment with BamH I/Not I, and ligating the double digested plasmid with EcoR I/Sph I to obtain the allele-replaced recombinant vector.

In an embodiment of the present disclosure, the transformation in the step (3) is an electrotransformation process.

The present disclosure also provides a recombinant strain obtained by the above-mentioned construction method.

The present disclosure provides use of the above-mentioned recombinant strain in the preparation of L-threonine.

The use of the recombinant strain in the preparation of L-threonine comprises fermenting the recombinant strain to prepare L-threonine.

DETAILED DESCRIPTION

The above-mentioned and other features and advantages of the present disclosure are explained and illustrated in more detail in the following description of examples of the present disclosure. It should be understood that the following examples are intended to illustrate the technical solutions of the present disclosure, and are not intended to limit the protection scope of the present disclosure defined in the claims and equivalents thereof in any way.

Unless otherwise indicated, the materials and reagents herein are either commercially available or can be prepared by one skilled in the art in light of the prior art.

Example 1

(1) Construction of Plasmid pKOV-deoB$^{(G1049A)}$ with deoB Gene Coding Region Having Site-Directed Mutation (G1049A) (Equivalent to that cysteine is substituted with tyrosine at the 350$^{th}$ Site (C350Y) in a Protein-Coding Amino Acid Sequence SEQ ID NO: 3, the Substituted Amino Acid Sequence being SEQ ID NO: 4)

Pentose phosphate mutase was encoded by a deoB gene, and in an *E. coli* K12 strain and a derivative strain thereof (such as MG1655), an ORF sequence of the wild-type deoB gene is shown in a sequence 3902352-3903575 in GenBank accession No. CP032667.1. Two pairs of primers for amplifying deoB were designed and synthesized according to the sequence, and a vector was constructed for a base G mutating to a base A at the 1049$^{th}$ site in a deoB gene coding region sequence (in SEQ ID NO: 1) of an original strain (to obtain a mutated nucleotide sequence SEQ ID NO: 2). The primers (synthesized by Shanghai Invitrogen Corporation) were designed as follows:

P1:
(SEQ ID NO: 5)
5' CGGGATCCATGGACGGCAACGCTGAAG 3'
(the underlined part is a restriction endonuclease cutting site BamH I);

P2:
(SEQ ID NO: 6)
5' GATCGTAACCGTGGTCAG 3';

P3:
(SEQ ID NO: 7)
5' CTGACCACGGTTACGATC 3';
and

P4:
(SEQ ID NO: 8)
5' AAGGAAAAAAGCGGCCGCGCTCGTGAGTGCGGATGT 3'
(the underlined part is a restriction endonuclease cutting site Not I).

The construction method was as follows: using primers P1/P2 and P3/P4 for PCR amplification by taking a wild-type gene of *E. coli* K12 as a template to obtain two DNA fragments having a length of 836 bp and 890 bp and point mutation (deoB$^{(G1049A)}$-Up and deoB$^{(G1049A)}$-Down fragments). PCR system: 10×Ex Taq buffer 5 μL, dNTP mixture (2.5 mM each) 4 μL, MgCl$_2$ (25 mM) 4 μL, primers (10 pm) 2 μL each, template 1 μL, Ex Taq (5 U/μL) 0.25 μL, total volume 50 μL, wherein the PCR amplification was performed as follows: pre-denaturing at 94° C. for 5 min, (denaturing at 94° C. for 30 s, annealing at 52° C. for 30 s, and extending at 72° C. for 90 s, for 30 cycles), and over-extension at 72° C. for 10 min. The two DNA fragments were separated and purified by agarose gel electrophoresis, and then the two purified DNA fragments were taken as templates, and P1 and P4 were taken as primers to perform overlap PCR to obtain a fragment (deoB$^{(G1049A)}$-Up-Down) having a length of about 1726 bp. Overlap PCR system: 10×Ex Taq buffer 5 μL, dNTP mixture (2.5 mM each) 4 μL, MgCl$_2$ (25 mM) 4 μL, primers (10 pm) 2 μL each, template 1 μL, Ex Taq (5 U/μL) 0.25 μL, total volume 50 μL, wherein the PCR amplification was performed as follows: pre-denaturing at 94° C. for 5 min, (denaturing at 94° C. for 30 s, annealing at 52° C. for 30 s, and extending at 72° C. for 90 s, for 30 cycles), and over-extension at 72° C. for 10 min. The deoB$^{(G1049A)}$-Up-Down fragment was separated and purified by agarose gel electrophoresis, then the purified fragment and a pKOV plasmid (purchased from Addgene) were double digested with BamH I/Not I, and the digested deoB$^{(G1049A)}$-Up-Down fragment and the digested pKOV plasmid were separated and purified by agarose gel electrophoresis followed by ligation to obtain a vector pKOV-deoB$^{(G1049A)}$. The vector pKOV-deoB$^{(G1049A)}$ was sent to a sequencing company for sequencing and identification, and the result is shown in SEQ ID NO: 11. The vector pKOV-deoB$^{(G1049A)}$ with the correct point mutation (deoB$^{(G1049A)}$) was stored for later use.

(2) Construction of Engineered Strain with deoB$^{(G1049A)}$ Having Point Mutation A wild-type deoB gene was reserved on chromosomes of a wild-type *Escherichia coli* strain *E. coli* K12 (W3110) and a high-yield L-threonine production strain *E. coli* CGMCC 7.232 (preserved in China General Microbiological Culture Collection Center). The constructed plasmid pKOV-deoB$^{(G1049A)}$ was transferred into *E. coli* K12 (W3110) and *E. coli* CGMCC 7.232, respectively, and through allele replacement, the base G mutated to the base A at the 1049$^{th}$ site of the deoB gene sequences in the chromosomes of the two strains as shown in SEQ ID NO: 1.

The specific process was as follows: transforming the plasmid pKOV-deoB$^{(G1049A)}$ into host bacterium competent cells through an electrotransformation process, and adding the cells into 0.5 mL of a SOC liquid culture medium; resuscitating the mixture in a shaker at 30° C. and 100 rpm for 2 h; coating an LB solid culture medium having a chloramphenicol content of 34 mg/mL with 100 μL of the culture solution, and culturing at 30° C. for 18 h; selecting grown monoclonal colonies, inoculating the colonies in 10 mL of an LB liquid culture medium, and culturing at 37° C. and at 200 rpm for 8 h; coating an LB solid culture medium having a chloramphenicol content of 34 mg/mL with 100 μL of the culture solution, and culturing at 42° C. for 12 h; selecting 1-5 single colonies, inoculating the colonies in 1 mL of an LB liquid medium, and culturing at 37° C. and 200 rpm for 4 h; coating an LB solid culture medium containing 10% of sucrose with 100 μL of the culture solution, and culturing at 30° C. for 24 h; selecting monoclonal colonies, and streaking the colonies on an LB solid culture medium having a chloramphenicol content of 34 mg/mL and an LB solid culture medium in a one-to-one correspondence manner; and selecting strains which grew on the LB solid culture medium and could not grow on the LB solid culture medium having the chloramphenicol content of 34 mg/mL for PCR amplification identification. The primers (synthesized by Shanghai Invitrogen Corporation) for use in PCR amplification were as follows:

```
P5:
                                    (SEQ ID NO: 9)
5' TGACGCCACCATCAAAGAGA 3';
and P6:
                                    (SEQ ID NO: 10)
5' GTCAACGCTCCGCCCAAAT 3'.
```

SSCP (Single-Strand Conformation Polymorphism) electrophoresis was performed on the PCR-amplified product; the amplified fragment of the plasmid pKOV-deoB$^{(G1049A)}$ was taken as a positive control, the amplified fragment of the wild-type *Escherichia coli* was taken as a negative control, and water was taken as a blank control. In SSCP electrophoresis, single-stranded oligonucleotide chains having the same length but different sequence arrangements formed different spatial structures in an ice bath and also had different mobilities during electrophoresis. Therefore, the fragment electrophoresis position was not consistent with that of negative control, and a strain having a fragment electrophoresis position consistent with that of positive control is the successfully allele-replaced strain. PCR amplification was performed on the target fragment by taking the successfully allele-replaced strain as a template and using primers P5 and P6, and then the target fragment was ligated to a pMD19-T vector for sequencing. Through sequence comparison of a sequencing result, the sequencing result is shown in SEQ ID NO: 12, and a recon formed by the base G mutating to the base A at the 1049$^{th}$ site in the deoB gene coding region sequence is the successfully modified strain. The recon derived from *E. coli* K12 (W3110) was named as YPThr09, and the recon derived from *E. coli* CGMCC 7.232 was named as YPThr10.

(3) Threonine Fermentation Experiment

The *E. coli* K12 (W3110) strain, the *E. coli* CGMCC 7.232 strain, and the mutant strains YPThr09 and YPThr10 were inoculated in 25 mL of a liquid culture medium described in Table 1, respectively, and cultured at 37° C. and 200 rpm for 12 h. Then, 1 mL of the resulting culture of each strain was inoculated in 25 mL of a liquid culture medium described in Table 1, and subjected to fermentation culture at 37° C. and 200 rpm for 36 h. The content of L-threonine was determined by HPLC, three replicates of each strain were taken, the average was calculated, and the results are shown in Table 2.

TABLE 1

| Culture medium formula | |
| --- | --- |
| Component | Formula g/L |
| Glucose | 40 |
| Ammonium sulfate | 12 |
| Potassium dihydrogen phosphate | 0.8 |
| Magnesium sulfate heptahydrate | 0.8 |
| Ferrous sulfate heptahydrate | 0.01 |
| Manganese sulfate monohydrate | 0.01 |

TABLE 1-continued

| Culture medium formula | |
| --- | --- |
| Component | Formula g/L |
| Yeast extract | 1.5 |
| Calcium carbonate | 0.5 |
| L-methionine | 0.5 |
| pH value adjusted with potassium hydroxide | pH 7.0 |

TABLE 2

| Threonine fermentation results | | | |
| --- | --- | --- | --- |
| Strains | Fermentation volume (g/L) | Mean value (g/L) | Multiple of improvement |
| *E. coli* K12 (W3110) | 0.01 0.02 0.00 | 0.01 | — |
| YPThr09 | 3.3 3.2 3.3 | 3.3 | 330 |
| *E. coli* CGMCC 7.232 | 16.6 16.5 16.8 | 16.6 | — |
| YPThr10 | 19.3 19.6 19.4 | 19.4 | 16.9% |

As can be seen from the results of Table 2, the substitution of cysteine at the 350$^{th}$ site of the amino acid sequence of the deoB gene with tyrosine contributes to the improvement of the yield of L-threonine for the original strain producing L-threonine with either high or low yield.

Example 2

(1) Construction of Transformation Vector pKOV-PrhtA$^{(A(-67)G)}$ with rhtA Gene Promoter Having Site-Directed Mutation Threonine and homoserine efflux proteins (RHTA enzymes) were encoded by rhtA genes, and in an *E. coli* K12 strain and a derivative strain thereof (e.g., W3110), a wild-type rhtA gene promoter sequence PrhtA was shown in a sequence 850520-850871 in GenBank accession No. AP009048.1.

According to this sequence, two pairs of primers for amplifying promoter PrhtA were designed and synthesized, and a vector was constructed for a base A mutating to a base G at the −67$^{th}$ site at the upstream of a base sequence (SEQ ID NO: 13) of the PrhtA promoter of an original strain (to obtain a nucleotide sequence SEQ ID NO: 14). The primers (synthesized by Shanghai Invitrogen Corporation) were designed as follows:

```
P1:
                                    (SEQ ID NO: 17)
5' CGGGATCCTCGCTGGTGTCGTGTTTGTAGG 3'
(the underlined part is a restriction endonuclease
cutting site BamH I);

P2:
                                    (SEQ ID NO: 18)
5' TATACCCAATGCTGGTCGAG 3';

P3:
                                    (SEQ ID NO: 19)
5' CGACCAGCATTGGGTATATC 3';
and
```

-continued

P4:
(SEQ ID NO: 20)
5' AAGGAAAAAAGCGGCCGCCGAAAATTAACGCTGCAATCAAC 3'
(the underlined part is a restriction endonuclease cutting site Not I).

The construction method was as follows: using primers P1/P2 and P3/P4 for PCR amplification by taking a genome of E. coli K12 as a template to obtain two DNA fragments having a length of 690 bp and 640 bp and point mutation (PrhtA$^{(A(-67)G)}$-Up and PrhtA$^{(A(-67)G)}$-Down fragments). PCR system: 10×Ex Taq buffer 5 μL, dNTP mixture (2.5 mM each) 4 μL, Mg$^{2+}$ (25 mM) 4 μL, primers (10 pM) 2 μL each, Ex Taq (5 U/μL) 0.25 μL, total volume 50 μL, wherein the PCR amplification was performed as follows: pre-denaturing at 94° C. for 5 min, (denaturing at 94° C. for 30 s, annealing at 52° C. for 30 s, and extending at 72° C. for 30 s, for 30 cycles), and over-extending at 72° C. for 10 min.

The two DNA fragments were separated and purified by agarose gel electrophoresis, and then the two purified DNA fragments were taken as templates, and P1 and P4 were taken as primers to perform overlap PCR to obtain a fragment (PrhtA$^{(A(-67)G)}$-Up-Down) having a length of about 1310 bp.

PCR system: 10×Ex Taq buffer 5 μL, dNTP mixture (2.5 mM each) 4 μL, Mg$^{2+}$ (25 mM) 4 μL, primers (10 pM) 2 μL each, Ex Taq (5 U/μL) 0.25 μL, total volume 50 μL, wherein the overlap PCR was performed as follows: denaturing at 94° C. for 30 s, annealing at 52° C. for 30 s, and extending at 72° C. for 60 s (for 30 cycles).

The PrhtA$^{(A(-67)G)}$-Up-Down fragment was separated and purified by agarose gel electrophoresis, then the purified fragment and a pKOV plasmid (purchased from Addgene) were double digested with BamH I/Not I, and the digested PrhtA$^{(A(-67)G)}$-Up-Down fragment and the digested pKOV plasmid were separated and purified by agarose gel electrophoresis followed by ligation to obtain a vector pKOV-PrhtA$^{(A(-67)G)}$. The vector pKOV-PrhtA$^{(A(-67)G)}$ was sent to a sequencing company for sequencing and identification, and the vector pKOV-PrhtA$^{(A(-67)G)}$ with the correct point mutation (PrhtA$^{(A(-67)G)}$) was stored for later use.

(2) Construction of Engineered Strain with PrhtA$^{(A(-67)G)}$ Having Point Mutation A wild-type PrhtA promoter was reserved on chromosomes of a wild-type Escherichia coli strain E. coli K12 (W3110) and a high-yield L-threonine production strain E. coli CGMCC 7.232 (preserved in China General Microbiological Culture Collection Center). The constructed plasmid pKOV-PrhtA$^{(A(-67)G)}$ was transferred into E. coli K12 (W3110) and E. coli CGMCC 7.232, respectively, and through allele replacement, the base A mutated to the base G at the –67$^{th}$ site at the upstream of base sequences of the PrhtA promoters in the chromosomes of the two strains.

The specific process was as follows: transforming the plasmid pKOV-PrhtA$^{(A(-67)G)}$ into host bacterium competent cells through an electrotransformation process, and adding the cells into a 0.5 mL SOC liquid culture medium; resuscitating the mixture in a shaker at 30° C. and 100 rpm for 2 h; coating an LB solid culture medium having a chloramphenicol content of 34 μg/mL with 100 μL of the culture solution, and culturing at 30° C. for 18 h; selecting grown monoclonal colonies, inoculating the colonies in a 10 mL LB liquid culture medium, and culturing at 37° C. and at 200 rpm for 8 h; coating an LB solid culture medium having a chloramphenicol content of 34 μg/mL with 100 μL of the culture solution, and culturing at 42° C. for 12 h; selecting 1-5 single colonies, inoculating the colonies in 1 mL of an LB liquid medium, and culturing at 37° C. and 200 rpm for 4 h; coating an LB solid culture medium containing 10% of sucrose with 100 uL of the culture solution, and culturing at 30° C. for 24 h; selecting monoclonal colonies, and streaking the colonies on an LB solid culture medium having a chloramphenicol content of 34 μg/mL and an LB solid culture medium in a one-to-one correspondence manner; and selecting strains which grew on the LB solid culture medium and could not grow on the LB solid culture medium having the chloramphenicol content of 34 μg/mL for PCR amplification identification. The primers (synthesized by Shanghai Invitrogen Corporation) for use in PCR amplification were as follows:

P5:
(SEQ ID NO: 21)
5' ATACACCGCTATCCATCT 3';
and

P6:
(SEQ ID NO: 22)
5' AACCAGGCATCCTTTCTC 3'.

PCR system: 10×Ex Taq buffer 5 μL, dNTP mixture (2.5 mM each) 4 μL, Mg$^{2+}$ (25 mM) 4 μL, primers (10 pM) 2 μL each, Ex Taq (5 U/μL) 0.25 μL, total volume 50 μL, wherein the PCR amplification was performed as follows: pre-denaturing at 94° C. for 5 min, (denaturing at 94° C. for 30 s, annealing at 52° C. for 30 s, and extending at 72° C. for 30 s, for 30 cycles), and over-detending at 72° C. for 10 min. SSCP (Single-Strand Conformation Polymorphism) electrophoresis was performed on the PCR-amplified product; the amplified fragment of the plasmid pKOV-PrhtA$^{(A(-67)G)}$ was taken as a positive control, the amplified fragment of the wild-type Escherichia coli was taken as a negative control, and water was taken as a blank control. In SSCP electrophoresis, single-stranded oligonucleotide chains having the same length but different sequence arrangements formed different spatial structures in an ice bath and also had different mobilities during electrophoresis. Therefore, the fragment electrophoresis position was not consistent with that of negative control, and a strain having a fragment electrophoresis position consistent with that of positive control is the successfully allele-replaced strain. PCR amplification was performed on the target fragment by taking the successfully allele-replaced strain as a template and using primers P5 and P6, and then the target fragment was ligated to a pMD19-T vector for sequencing. Through sequence comparison of a sequencing result, a recon formed by the base A mutating to the base G at the –67$^{th}$ site at the upstream of the base sequence of the PrhtA promoter is the successfully modified strain. The recon derived from E. coli K12 (W3110) was named as YPThr01, and the recon derived from E. coli CGMCC 7.232 was named as YPThr 02.

(3) Threonine Fermentation Experiment

The E. coli K12 (W3110) strain, the E. coli CGMCC 7.232 strain, and the mutant strains YPThr01 and YPThr02 were inoculated in 25 mL of a liquid culture medium described in Table 1, and cultured at 37° C. and 200 rpm for 12 h. Then, 1 mL of the resulting culture of each strain was inoculated in 25 mL of a liquid culture medium described in Table 1, and subjected to fermentation culture at 37° C. and 200 rpm for 36 h. The content of L-threonine was determined by HPLC, three replicates of each strain were taken, the average was calculated, and the results are shown in Table 2.

TABLE 1

Culture medium formula

| Component | Formula g/L |
| --- | --- |
| Glucose | 40 |
| Ammonium sulfate | 12 |
| Potassium dihydrogen phosphate | 0.8 |
| Magnesium sulfate heptahydrate | 0.8 |
| Ferrous sulfate heptahydrate | 0.01 |
| Manganese sulfate monohydrate | 0.01 |
| Yeast extract | 1.5 |
| Calcium carbonate | 0.5 |
| L-methionine | 0.5 |
| pH value adjusted with potassium hydroxide | pH 7.0 |

TABLE 2

Threonine fermentation results

| Strains | Fermentation volume (g/L) | Mean value (g/L) | Multiple of improvement |
| --- | --- | --- | --- |
| E. coli K12 (W3110) | 0.02<br>0.02<br>0.03 | 0.02 | — |
| YPThr01 | 1.8<br>1.9<br>1.7 | 1.8 | 90 |
| E. coli CGMCC 7.232 | 16.1<br>16.2<br>16.2 | 16.2 | — |
| YPThr02 | 18.3<br>18.1<br>17.7 | 18.0 | 11.1% |

As can be seen from the results of Table 2, the mutation of the base A at the $-67^{th}$ site of the promoter sequence of the rhtA gene to the base G contributes to the improvement of the yield of L-threonine for the original strain producing L-threonine with either high or low yield.

The examples of the present disclosure have been described above. However, the present disclosure is not limited to the above examples. Any modification, equivalent, improvement and the like made without departing from the spirit and principle of the present disclosure shall fall within the protection scope of the present disclosure.

The invention claimed is:

1. A promoter nucleotide consisting of the sequence shown in SEQ ID NO: 14.

2. A nucleic acid molecule consisting of the promoter sequence shown in SEQ ID NO: 14 and a rhtA gene.

3. An expression cassette comprising the nucleic acid molecule according to claim 2.

4. A recombinant vector comprising the nucleic acid molecule according to claim 2.

5. The recombinant vector according to claim 4, wherein the recombinant vector is constructed by introducing the nucleic acid molecule into a plasmid.

6. A recombinant bacterial strain, comprising the nucleic acid molecule according to claim 2.

7. The recombinant bacterial strain according to claim 6, wherein the recombinant bacterial strain is *Escherichia coli*.

8. A method for constructing the recombinant bacterial strain according to claim 6, comprising the following steps:
   (1) modifying the nucleotide sequence of the wild-type gene shown in SEQ ID NO: 13 to obtain a mutated nucleotide sequence shown in SEQ ID NO: 14;
   (2) ligating the mutated nucleotide sequence to a plasmid to construct a recombinant vector; and
   (3) introducing the recombinant vector into a host bacterial strain to obtain the recombinant bacterial strain.

9. A method of preparing L-threonine, comprising fermenting the recombinant bacterial strain according to claim 8 in a liquid culture medium consisting of: 40 g/L glucose, 12 g/L ammonium sulfate, 0.8 g/L potassium dihydrogen phosphate, 0.8 g/L magnesium sulfate heptahydrate, 0.01 g/L ferrous sulfate heptahydrate, 0.01 g/L manganese sulfate monohydrate, 1.5 g/L yeast extract, 0.5 g/L calcium carbonate, and 0.5 g/L L-methionine.

10. The expression cassette according to claim 3, wherein the rhtA gene is SEQ ID NO: 15.

11. The recombinant bacterial strain according to claim 7, wherein the *Escherichia coli* is *E. coli* K12, *E. coli* K12 substrain W3110, or *E. coli* CGMCC 7.232.

* * * * *